United States Patent [19]

Kjørnes et al.

[11] Patent Number: 4,713,248
[45] Date of Patent: Dec. 15, 1987

[54] DIFFUSION COATED MULTIPLE-UNITS DOSAGE FORM

[75] Inventors: Kim Kjornæs, Valby; Jørgen Linnemann, Dragør, both of Denmark

[73] Assignee: A/S Alfred Benzon, Copenhagen, Denmark

[21] Appl. No.: 786,967

[22] PCT Filed: Feb. 8, 1985

[86] PCT No.: PCT/DK85/00006
§ 371 Date: Oct. 4, 1985
§ 102(e) Date: Oct. 4, 1985

[87] PCT Pub. No.: WO85/03437
PCT Pub. Date: Aug. 15, 1985

[30] Foreign Application Priority Data
Feb. 10, 1984 [DK] Denmark ............... 621/84

[51] Int. Cl.⁴ ............... A61K 9/14; A61K 9/22
[52] U.S. Cl. ............... 424/468; 427/3; 424/469; 424/470
[58] Field of Search ............... 427/3; 424/19, 20, 21, 424/35, 38, 468, 469, 470

[56] References Cited

U.S. PATENT DOCUMENTS

| | | | |
|---|---|---|---|
| 2,928,770 | 3/1960 | Bardani | 424/22 |
| 2,991,226 | 7/1961 | Millar et al. | 424/21 |
| 3,431,338 | 3/1969 | Munzel | 424/21 |
| 3,437,728 | 4/1969 | Renwanz | 424/21 |
| 4,017,647 | 4/1977 | Ohno et al. | 427/3 |
| 4,178,361 | 12/1979 | Cohen et al. | 424/22 |
| 4,193,985 | 3/1980 | Bechgaard et al. | 424/2 |
| 4,259,315 | 3/1981 | Lippmann et al. | 424/20 |
| 4,292,302 | 9/1981 | Keith et al. | 424/22 |
| 4,361,546 | 11/1982 | Stricker et al. | 424/20 |
| 4,432,966 | 2/1984 | Zeitoun et al. | 424/21 |

FOREIGN PATENT DOCUMENTS

| | | |
|---|---|---|
| 13262 | 7/1980 | European Pat. Off. |
| 63014 | 10/1982 | European Pat. Off. |
| 53-139715 | 12/1978 | Japan |
| 1468172 | 3/1977 | United Kingdom |
| 2066070 | 7/1981 | United Kingdom |

Primary Examiner—Ronald W. Griffin
Attorney, Agent, or Firm—Stiefel, Gross, Kurland & Pavane

[57] ABSTRACT

In an oral pharmaceutical controlled release multiple-units formulation, individual units containing an active substance are coated with a substantially water-insoluble, but water-diffusible controlled release coating which includes
(1) an inner film layer comprising a homogeneous combination of a water-dispersible film-forming agent and a polymeric substance which imparts compressibility to the coating, and
(2) optionally an outer film layer comprising a film-forming agent which prevents adhesion between the units at elevated temperatures and imparts flowability to the units.

The coating possesses a sufficient plastic deformability to result in no significant changes in the release characteristics of compressed coated units relative to non-compressed coated units.

15 Claims, 2 Drawing Figures

1

DIFFUSION COATED MULTIPLE-UNITS DOSAGE FORM

The present invention relates to an oral pharmaceutical controlled release multiple-units dosage form in which individual units containing an active substance are coated with a water-based diffusion coating.

TECHNICAL BACKGROUND

Many physiological factors influence both the gastrointestinal transit time and the release of a drug from a controlled release dosage form and thus the uptake of the drug into the systemic circulation. Dosage forms should therefore be designed so that such variable factors do not compromise the efficacy and safety of the product.

In humans, a reproducible gastrointestinal transit time of a depot formulation can be achieved only by a controlled release multiple-units dosage form.

The term "controlled release multiple-units formulation" (Bechgaard & Hegermann Nielsen, 1978) indicates a pharmaceutical formulation comprising a multiplicity (typically at least 100) of individual coated (or "microencapsulated") units contained in the formulation in such a form that the individual units will be made available from the formulation upon disintegration of the formulation in the stomach of animals, including humans, who have ingested the formulation. Typically, the multiple-units formulation may be a capsule which disintegrates in the stomach to make available a multiplicity of individual coated units contained in the capsule, or a tablet which disintegrates in the stomach to make available a multiplicity of coated units originally combined in the tablet.

Drug release from a controlled release dosage form is generally controlled either by diffusion through a coating or by erosion of a coating by a process dependent on, e.g., enzymes or pH. The importance of a pH independent diffusion with respect to obtaining a reproducible rate of availability and to minimizing intra- and intersubject variations is known (GB Patent No. 1 468 172 and Bechgaard & Baggesen, 1980). It is also known that controlled drug release in vivo can be achieved through an erodable process by enteric coating of a multiple-units dosage form (Green, 1966; McDonald et al., 1977; Bogentoft et al., 1978).

Both above-mentioned types of controlled release multiple-units formulation techniques aim at a controlled release of active substance in a predetermined pattern to reduce and delay the peak plasma concentration without affecting the extent of drug availability. Due to a lower peak plasma concentration, the frequency of undesirable sideeffects may be reduced, and due to the delay in the time it takes to obtain the peak plasma concentration and the prolongation of the time at the therapeutically active plasma concentration, the dosage frequency may be reduced to a dosage taken only twice or once a day, in order to improve patient compliance.

A further advantage of the controlled release multiple-units dosage form is that high local concentrations of the active substance in the gastrointestinal system is avoided, due to the units being distributed freely throughout the gastrointestinal tract, independent of gastric emptying. If the mucosa of the stomach is more sensitive to the active substance than the intestinal mucosa, controlled release formulations avoiding release of active substance in the gastric area will be preferred; formulations of this type are controlled release multiple-units formulations in which the coatings are substantially resistant to gastric conditions.

The present invention deals with multiple-units dosage forms which are diffusion-coated.

In the known art preparations of diffusion-coated controlled release multiple-units formulations, diffusion film-coating mixtures have been used which contain synthetic film-forming agents dissolved or dispersed in organic solvents, e.g. isopropanol, ethanol, acetone, or mixtures thereof. However, although these mixtures show advantages in that the film-forming agents are diffusion controlling per se, that is, without any modification or addition, and the film formed is nontacky, they suffer from serious disadvantages from an environmental and process-economic point of view:

The use of organic solvents gives rise to environmental pollution, danger of explosion, and health hazards unless costly recycling procedures are used, such as recycling in scrubber towers, and the fact that the film coating mixtures have a low dry matter content (normally less than 15% by weight), incurs long processing periods resulting in a low process efficiency.

From an environmental and process-economic point of view, water-based film-coating mixtures are more desirable; the present invention concerns developments relating to water-based film coatings.

DISCLOSURE OF THE INVENTION

Figure 1:
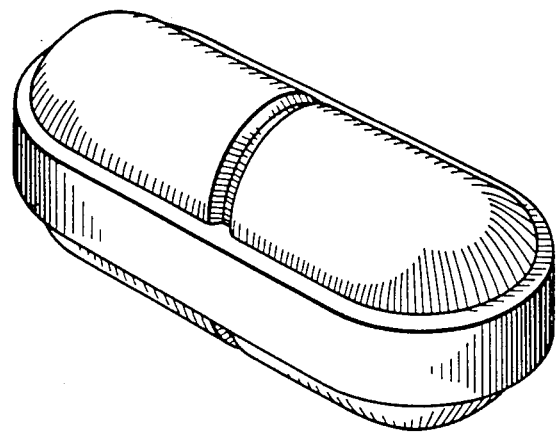
FIG. 1 and FIG. 2 both show tablets having a shape substantially corresponding to a cylinder with rounded ends, a raised area circumscribing the periphery of the cylinder in the form of a flat belt and a score dividing the cylinder, but not the peripheral belt, into two parts.
Figure 2:
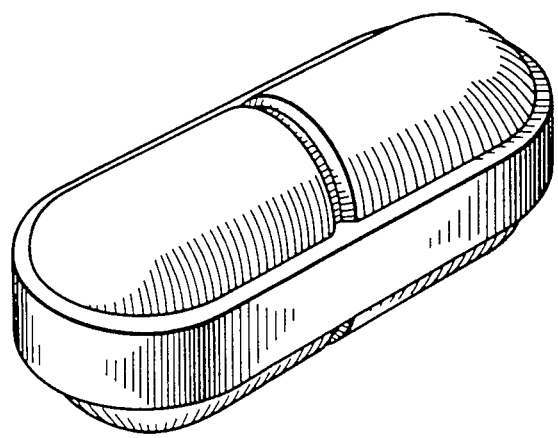

The present invention provides an oral pharmaceutical controlled release multiple-units formulation in which individual units containing an active substance are coated with a substantially water-insoluble, but water-diffusible controlled release coating which includes (1) an inner film layer comprising a homogeneous combination of a water-dispersible film-forming agent and a polymeric substance which imparts compressibility to the coating, and (2) optionally an outer film layer comprising a film-forming agent which prevents adhesion between the units at elevated temperatures and imparts flowability to the units.

As appears from the experimental data given in the examples, it has surprisingly been found that addition of a polymeric substance, which is capable of forming a continuous phase to a water-dispersible filmforming agent will result in a coating which delays and controls the diffusion through the inner film layer in a useful and reproducible manner to confer desirable controlled release characteristics to the coated units and that this coating is furthermore compressible. In the present context, the term "compressibility" when used to describe a property of the coating refers to a coating possessing a sufficient plastic deformability to result in no significant changes in the release characteristics of compressed coated units relative to non-compressed coated units. It has surprisingly been found that such compressibility may be provided by homogeneously mixing the film-forming agent with a polymeric substance which functions as a reinforcing agent by imparting greater hardness as well as plastic deformability to the layer. In the present context, the term "capable of forming a continuous phase" is intended to indicate that the polymeric substance is capable, in itself, that is, without admixture with other components, of forming a continuous phase (that is, by being molten or by being dissolved and subjected to removal of the solvent), and that it forms a homogeneous lattice-like structure in the inner layer. The term "homogeneous" is intended to indicate that, throughout the inner layer, the two components are present in the same proportions and uniformly distributed in each other. In the present context, the term "diffusion coating" indicates a coating which does not disintegrate or dissolve in water, but which gradually lets the active substance in the units pass through. The term is intended to include the so-called enteric coatings which at an acid pH have properties similar to those of the conventional diffusion coatings.

The water-dispersible film-forming agents contemplated for the purpose of the present invention are pharmaceutically acceptable filmforming polymers which are substantially water-insoluble, but which permit water diffusion. Examples of such substances are cellulose derivatives, silicone polymers and copolymers, vinyl polymers and copolymers, acrylic polymers and copolymers and biodegradable polymers such as polyamino acids, polylactic acid and copolymers and derivatives thereof, or mixtures thereof. More specifically, the filmforming substance is selected from ethylcellulose and a copolymerisate of anionic or non-ionic poly(-meth)acrylic acid esters, hydroxypropylmethylcellulosephthalate, celluloseacetatephthalate, polyvinylacetatephthalate and vinylacetate-crotonic acid copolymerisates.

The polymeric substance incorporated according to the invention may be any pharmaceutically acceptable polymeric substance which will bring about the desired compressibility of the coating. The amount of the polymeric substance incorporated will depend on the properties of the polymeric substance, in particular its film-forming properties and its hardness and plasticity. Apart from this, it is important that the polymeric substance is one which contributes to imparting anti-adhesive properties to the inner film layer during coating.

The polymeric substance incorporated in the inner film layer is preferably a water-soluble polymeric substance as substances which are precipitated from an aqueous solution during the coating process are more easily homogeneously admixed with the film-forming agent in the inner film layer. Typical examples of such polymeric substances are polyvinylpyrrolidone, polyalkylene glycols such as polyethylene glycol, and cellulose derivatives such as hydroxypropylcellulose, carboxymethylcellulose, methylcellulose, propylcellulose, hydroxyethylcellulose, carboxyethylcellulose, carboxymethylhydroxyethylcellulose, hydroxymethylcellulose, carboxymethylethylcellulose, methylhydroxypropylcellulose or hydroxypropylmethylcellulose.

The polymeric substance will normally be present in the inner film layer in an amount of between about 1 and 10%, in particular between about 2 and 8%, especially about 4%, by weight relative to the amount of film-forming agent in the inner film layer. If the substance is a water-soluble substance, such as one of those mentioned above, it is important not to incorporate it in amounts which would significantly reduce or even destroy the sustained release effect.

According to the invention, it has also been found that in some cases it is advantageous to include an additional anti-adhesive in the inner film layer. Due to the anti-adhesive effect of the polymeric substance, however, it is only necessary to add small amounts of this anti-adhesive (if any), which is desirable as the anti-adhesives usually employed for the present purpose do not contribute to the desired sustained release and often necessitate the use of larger amounts of coating material which, in turn, prolongs the coating process. The additional anti-adhesive is preferably a finely divided, substantially insoluble, pharmaceutically acceptable non-wetting powder having anti-adhesive properties in the coating. Examples of anti-adhesives are metallic stearates such as magnesium stearate or calcium stearate, microcrystalline cellulose, or mineral substances such as calcite, substantially water-insoluble calcium phosphates or substantially waterinsoluble calcium sulfates, colloidal silica, titanium dioxide, barium sulfates, hydrogenated aluminium silicates, hydrous aluminum potassium silicates and talc. The preferred anti-adhesive is talc. The anti-adhesive, e.g. talc, is preferably incorporated in the coating in an amount of between about 1 and 50% by weight, in particular between about 5 and 30% by weight, and preferably about 15%, by weight of the inner film layer. The particle size of the anti-adhesive should normally be below about 40 $\mu$m, as by selecting a small particle size a larger surface area is obtained; the consequent higher anti-adhesive effect makes it possible to incorporate smaller amounts of anti-adhesive. The particle size should also be adapted so as to prevent sedimentation of the anti-adhesive in the coating mixture or blocking of jets and tubes in the coating equipment.

It has been found that the coagulation of the film-forming agent is sterically hindered by the polymeric substance so that such coagulation and consequently formation of a continuous phase proper of the film-forming agent will only occur over a longer period of time. This means that it is not possible to maintain a reproducible release rate of the active substance as a decreasing release rate has been observed for such coatings. It has surprisingly been found that by heating the units the coagulation of the film-forming agent is accelerated so that the coating no longer changes its diffusion characteristics in the course of time, whereby storage stability is imparted to the pharmaceutical composition comprising units coated as specified above.

It may be possible to perform the heating without taking further measures, as several film-forming agents of the type employed in the present invention may be heated to the desired temperature without this involving any processing difficulties. Many film-forming agents, however, may exhibit a tendency to become tacky on heating, so that, in these cases, it may be necessary to provide the units with an additional, protective layer which is composed of a substance or mixture of substances which is anti-adhesive at elevated temperatures and, preferably, also imparts flowability to the coated units.

As a general rule, the film-forming agent in the outer film layer is one which is anti-adhesive at temperatures above about 40° C., especially temperatures above about 50° C., such as a temperature between about 60° C. and about 120° C. However, additional criteria may also be applied to select a film-forming agent with the desired properties. For instance, it may in some cases be advantageous to provide a further sustained release effect, so the outer layer may also function as an additional diffusion barrier throughout the gastrointestinal tract or be one which is dissolved in intestinal fluids only (an enteric coating). Furthermore, the outer layer may additionally contain an active substance which may either be the same substance as the one contained in the units, and which may for instance be designed for instant release, or which may be another drug advantageously administered simultaneously therewith. These additional characteristics are not vital, however, and suitable film-forming agents for this purpose are found within most categories of film-forming agents.

Examples of such agents are diffusion coating materials such as ethyl-cellulose or enteric coating materials such as anionic poly(meth)acrylic acid esters, hydroxypropylmethylcellulosephthalate, celluloseacetatephthalate, polyvinylacetatephthalate, polyvinylacetatephthalate-crotonic acid copolymerisates, or mixtures thereof, or water-soluble coating materials such as water-soluble cellulose derivatives, e.g. hydroxypropylcellulose, carboxymethylcellulose, methylcellulose, propylcellulose, hydroxyethylcellulose, carboxyethylcellulose, carboxymethylhydroxyethylcellulose, hydroxymethylcellulose, carboxymethylethylcellulose, methylhydroxypropylcellulose and hydroxyproplmethylcellulose. The currently favored film-forming agent for the outer layer is in fact hydroxypropylmethylcellulose although, as indicated above, it is water-soluble and thus does not contribute to delaying release. The layer of the protective film-forming agent need not be particularly thick, and is usually applied in an amount of about 0.1–10%, especially about 0.5–5%, in particular about 1% by weight of the uncoated units.

According to the invention, it has been found that the properties of the outer layer with respect to imparting improved flowability to the powder of the coated units may be considerably improved if a lubricant is incorporated therein in admixture with the film-forming agent. The lubricant is preferably present in the form of a finely divided, pharmaceutically acceptable powder, such as a metallic stearate, e.g. magnesium stearate or calcium stearate, microcrystalline cellulose, or a mineral substance such as titanium dioxide, calcite, calcium phosphate, calcium sulfate, colloidal silica, barium sulfates, hydrogenated aluminum silicates, or hydrous aluminum potassium silicates. Most preferably, the lubricant is talc.

The individual units of the multiple-units formulations according to the invention will normally be either coated crystals or pellets (coated cores). In the pellets, the core is constituted of a combination of active substance and excipients. A type of core which is widely used in the known art (vide, e.g., European Patent Application, Publication No. 0 013 262) is a substantially spherical particle of a size of about 0.5–1 mm consisting of excipient(s) with active substance applied to its surface. Typical cores of this type are the so-called "non-pareil" cores where the excipients are in the form of spherical particles of saccharose. It is also known, e.g., from GB Patent Specification No. 1 468 172, to prepare cores which are cross-sectionally substantially homogeneous. In the present context, the term "cores which are cross-sectionally substantially homogeneous" designates cores in which the active substance is not confined to an exterior layer on the core body, in other words normally cores which, through the cross-section of the core body, contain substantially the same type of composition comprising microparticles containing active substance, in contrast to the non-pareil type of cores which each consist of an excipient body with active substance applied to its surface, and in contrast to coated crystal units which are substantially monolithic crystals. From this definition, it will be understood that the cores which are cross-sectionally substantially homogeneous will normally consist of a mixture of active substance with excipient(s), (and in spite of the term "homogeneous", this mixture will not necessarily be qualitatively or quantitatively homogeneous through the cross-section of the particle but may show, e.g., a concentration gradient of one or more of its constituents) or they may consist substantially solely of active substance in a non-monolithic form, e.g. as a sintered mass of crystalline or amorphous particles of active substance. In the following specification and claims, such cores which are cross-sectionally substantially homogeneous will, for the sake of brevity, often simply be designated "cores".

The oral pharmaceutical controlled release multiple-units formulation according to the invention will typically be a capsule containing a multiplicity of the units, typically more than 100, a sachet containing a multiplicity of the units, typically more than 1000, or a tablet made from a multiplicity of the units, typically more than 100, in such a manner that the tablet will disintegrate substantially immediately upon ingestion in the stomach into a multiplicity of individual units which are distributed freely throughout the gastro-intestinal tract.

The pharmaceutical formulation of the invention may also be one in which units of the type described above, that is, diffusion coated units are combined with uncoated units which comprise the same or another active substance for instant release thereof, and/or with non-diffusion coated units which have been provided with a coating selected from hydrophilic coatings, hydrophobic coatings, water-based coatings and organic coatings imparting desired properties to the unit such as acid or alkali resistance, storage stability, taste masking, light stability, coloring, improved processability, etc. The ratio between diffusion coated and uncoated or non-diffusion coated units in the composition may be adjusted according to, for instance, the desired release characteristics of the composition, but is preferably in the range of about 10:90–90:10 of diffusion coated units to uncoated or non-diffusion coated units.

The formulations mentioned above may be prepared by conventional methods known in the pharmaceutical industry. One particularly interesting resting shape of a tablet according to the invention, in particular when the tablet is to contain a rather large amount of active substance and is to be easy to swallow, is a shape substantially corresponding to a cylinder with rounded ends, a raised area circumscribing the periphery of the cylinder in the form of a flat belt and a score dividing the cylinder, but not the peripheral belt, into two parts, substantially as shown in the drawing. As an example of such tablets may be mentioned tablets in which the active substance is potassium chloride crystals, e.g. in tablet sizes comprising 600 mg and 750 mg of potassium chloride, respectively, for use as potassium supplement for patients in diuretic treatment.

The invention also relates to a method for preparing an oral pharmaceutical controlled release multiple-units formulation in which (a) individual units containing an active substance are coated with a film-coating mixture comprising an aqueous dispersion of a filmforming agent and a polymeric substance which prevents adhesion between the units and which imparts compressibility to the inner film layer, (b) the thus coated units are optionally provided with an outer film layer of a film-forming agent which prevents adhesion between the units at elevated temperatures and imparts flowability to the coated units, and (c) the coated units are subsequently heated to a temperature at which the film-forming agent forms a continuous phase in homogeneous admixture with the polymeric substance, whereby a coating which does not change its diffusion characteristics in the course of time is formed.

DETAILED DESCRIPTION OF THE INVENTION

Cores

According to the invention, the cores are preferably cross-sectionally substantially homogeneous cores.

The cores are typically made by granulating particles of the active substance together with excipients, including bulk agents such as carbohydrates and derivatives thereof such as starch and starch derivatives, including microcrystalline cellulose, binders such as cellulose derivatives, including methylcellulose or hydroxypropylmethylcellulose, polyethylene glycol, polyvinylpyrrolidone, agar, or gelatin, for instance by treatment in a high speed mixer (to directly obtain compact-shaped cores), or by treatment in a planet mixer with subsequent extrusion of the mixture into strings of a predetermined diameter approaching the desired final cross-sectional dimension of the cores and treatment of the strings in a marumerizer or similar equipment to obtain compact-shaped cores. The diameter of the cores is normally adapted so that the diameter of the coated core is about 0.1–1.5 mm, in particular about 0.4–1.0 mm, e.g. about 0.4–0.7 or 0.7–1.0 mm.

Crystals

When the units coated according to the invention are crystals, they normally have a size between about 0.1 and 1.5 mm, preferably between about 0.4 and 1.0 mm. As an important example of an active substance which is suitably used in the form of crystals, potassium chloride may be mentioned.

Active Substance

The active substance in the formulations according to the invention may be any active substance which is advantageously administered in a controlled release multiple-units formulation. Examples of suitable active substances are found among almost all therapeutic groups, including diuretics, antiepileptics, sedatives, antiarrythmics, β-blockers, vasodilators, analgesics, bronchodilators, hormones, vitamins, oral antidiabetics, antibiotics, antihypertensives, antiinflammatory drugs, antimicrobial agents and antidepressants, polypeptides (enkephalines and endorphines), enzymes and mucopolysaccharides.

As examples of active substances may be mentioned pindolol, quinidine salts, lithium carbonate, acemetacin, vincamine, dipyridamol, theophylline, dextropropoxyphene, amitriptyline, hydralazine, digoxin, furosemide, propranolol, ibuprofen, lidocaine, mepyramine, nitroglycerin, clonidine, disopyramide, verapamil, captopril, prazocin, nifedipine, paracetamol and indomethacin.

Among these substances, some are characterized as having a pH dependent solubility, others as having a pH-independent solubility. Active substances having a pH-dependent solubility (that is, a solubility which differs corresponding to a ratio of $10:10^3$ over the physiological pH range of 1–7.5) are preferably incorporated in cores in combination with buffer substances such as discussed above, in order to obtain a dissolution of active substance which is substantially independent of the gastrointestinal pH variations through which the units pass.

Especially important formulations according to the invention are formulations in which the active substance, apart from being a substance about which it is known or indicated from a pharmacokinetic and/or clinical point of view that it is advantageously administered in a controlled release multiple-units formulation, is a substance which exerts an irritating effect on the gastrointestinal mucosa such as acetylsalicylic acid, potassium chloride, lithium salts, propionic acid derivatives, iron salts and magnesium salts.

In utilizing the principle of the invention, the units are freely distributed throughout the gastrointestinal tract, independent of gastric emptying, as the units are small enough to pass the pylorus even when the sphincter is closed. This makes it possible to obtain a low concentration at the mucosa and thus to minimize the risk of local irritation.

Coating

The diffusion coating (i.e. usually the inner film layer) applied on the units according to the invention is a diffusion coating which is applied from a dispersion in water. The application of the coating is typically performed in a fluidized bed or by pan coating.

Examples of diffusion coating materials which may be used for the purpose of the present invention are coatings selected from the group consisting of acrylic polymers and copolymers, e.g., a polymerisate of acrylic acid ethylesters and methacrylic acid methylester such as Eudragit ® E 30 D or ethylcellulose such as Aquacoat ® ECD-30. Enteric coating materials such as hydroxypropylmethylcellulosephthalate, e.g. HP 50 or HP 55, polyvinylacetatephthalate, e.g. Coateric ®, celluloseacetatephthalate and the like may also be employed according to the same principles.

In a preferred embodiment of the present invention, using a watersoluble polymer as the reinforcing agent, e.g. hydroxypropylmethylcellulose which in fact is the preferred substance, the coating mixture for the inner film layer is prepared by heating water to a temperature at which the hydroxypropylmethylcellulose is not soluble in water (i.e. a temperature above about 60° C.), the additional anti-adhesive such as talc is dispersed in the hot water, which is an advantage as, at the higher temperature, there is less surface tension, and the hydroxypropylmethylcellulose is dispersed in the mixture in the form of discrete particles. After dispersion, the mixture is slowly cooled to below about 60° C. with stirring so that the hydroxypropylmethylcellulose is dissolved. The film-forming agent is then added to the resulting cooled mixture with stirring until a homogeneous mixture is obtained.

The coating material may be admixed with various excipients such as plasticizers, inert fillers, and pigments, in a manner known per se.

Examples of plasticizers include triacetin, Myvacet ™ 9-40T (acetylated monoglyceride), rape oil, olive oil, sesame oil, acetyltributylcitrate, acetyltriethylcitrate, glycerin, sorbitol, diethyloxalate, diethylmalate, diethylfumarate, diethylsuccinate, diethylmalonate, diethyltartrate, tri-n-butylcitrate, dibutylphthalate, diethylphthalate, dioctylphthalate, dibutylsebacate, triethylcitrate, tributylcitrate, glyceroltributyrate, polyethyleneglycol, propyleneglycol, and mixtures thereof. The plasticizer is normally incorporated in an amount of 1–30%, calculated on the dry matter content of the coating mixture.

However, according to the invention, it has been found that for certain polymers, in particular an acrylic polymer such as a copolymerisate of acrylic acid ethylester and methacrylic acid methylester, a plasticizer may not be necessary, and hence, a particular aspect of the invention provides units coated with a plasticizer-free coating, in particular a coating based on a copolymerisate of acrylic acid ethylester and methacrylic acid methylester as the film-forming polymer, of the type according to the invention.

The amount of inner film layer applied is adapted so as to obtain a predetermined dissolution characteristic of the coated units. Normally, the amount of the inner film layer will be about 1–30% by weight, especially about 5–25%, particularly about 15%, by weight of the uncoated units depending on the predetermined dissolution characteristics of the active substance and the desired release profile.

The amount of dry matter in the film-coating mixture will normally be about 1–50%, especially 5–30%, and typically about 20%. It is advantageous to have a high dry matter content in the film-coating mixture as this reduces the coating time necessary to obtain an adequate coating of the units.

As mentioned above, hydroxypropylmethylcellulose is a preferred film-forming agent for the outer film layer. Apart from being antiadhesive at elevated temperatures, the currently preferred hydroxypropylmethylcellulose, e.g. Methocel ® E5 premium or Pharmacoat ® 606, has a low viscosity in an aqueous solution so that it is possible to obtain as high a dry matter content as 6–8%. This means that a reduction of the coating time is obtained for the outer film layer as well. When using hydroxypropylmethylcellulose, it may be advantageous to incorporate a plasticizer such as one of the plasticizers mentioned above. Similarly, surfactants, pigments and other conventional additives may be incorporated in a manner known per se.

Dosage forms

The units prepared according to the invention may be incorporated in normal pharmaceutical dosage forms or formulations such as capsules containing a multiplicity of the units, sachets containing a multiplicity of the units, or tablets which will disintegrate substantially immediately upon ingestion in the stomach to form a multiplicity of individual units.

In known pharmaceutical compositions of the multiple-units type coated with a water-based diffusion coating material and tabletted according to conventional techniques, an unacceptably high change in the release rate of the active substance has been observed, especially when the units are coated cores, while with pharmaceutical compositions according to the present invention which are also produced by conventional tabletting methods, only an insignificant and controllable change in the release rate, if any, has been observed, vide the appended examples.

Thus, the present invention further relates to a pharmaceutical composition in which the multiplicity of units are coated crystals or, most preferably, coated cores of the type defined above which are compressed to tablets with about 25–40% of conventional tabletting excipients to a tablet hardness of at least about 4 kp (as measured by means of a Schleuniger apparatus as described below) without any significant change in release characteristics relative to non-compressed units of the same composition.

The adjuvants and excipients used in the preparation of disintegratable tablets are of the same kind as conventionally used in the pharmaceutical industry for this purpose. Examples of filler or diluents useful for preparing tablets according to the invention are lactose, sucrose, dextrose, mannitol, calcium sulfate, dicalcium phosphate, tricalcium phosphate, starches such as rice starch and microcrystalline cellulose. Useful binders are acacia, tragacanth, gelatine, sucrose, pregelatinized starch, starch, sodium alginate, ammonium calcium alginate, methylcellulose, sodium carboxymethylcellulose, ethylcellulose hydroxypropylmethylcellulose, polyvinylpyrrolidone, magnesium aluminum silicate, and polyacrylamides. As examples of disintegrants may be mentioned cross-linked polyvinylpyrrolidone, starch derivatives such as sodium carboxymethylcellulose, and cellulose derivatives. As lubricants, "gliders" and "antiadhesives" may be mentioned metallic stearates, talc, high melting point waxes, and colloidal silica.

When it is desired to use excipients or adjuvants for the preparation of sachets or capsules, such as fillers and lubricants, these may be of the same type as described above.

The filling of capsules and sachets and the compression of tablets are performed in a manner known per se.

MATERIALS AND METHODS

In the examples, the following materials were used:
Sodium dihydrogen phosphate: Anhydrous. Analyzed according to BP 80.
Sucrose powder: Ph. Eur.
Microcrystalline cellulose: BPC 79. Avicel ® supplied by FMC, Philadelphia.
Talc: Ph. Eur. and additionally complying with the following requirements: About 0.002 g of talc is distributed in 1 drop of cyclohexanol and investigated under microscope. 45 particles out of 50 may not be above 40 μm.
Potassium chloride: Ph.Eur.
Hydroxypropylmethylcellulose: USP 20. Methocel ® E5 premium. Supplied by Dow Chemicals, Michigan, USA. Abbreviated to HPMC.
Propranolol hydrochloride: BP 80.
Sodium carboxymethylcellulose: USP 20. Blanose ® 7 LFD. Supplied by Hercules through Scandibutor, Copenhagen, Denmark.
Purified water: Ph. Eur.
Eudragit ® E 30 D: A neutral acrylic acid ethylester/methacrylic acid methylester copolymerisate in the ratio 70:30, molecular weight above 800,000, as a 30% aqueous dispersion, supplied by Röhm Pharma GmbH, Darmstadt, Germany.
Rice starch: Ph.Eur./USP 20.
Magnesium stearate: Ph.Eur./USP 20.

Determination of in vitro dissolution characteristics:
In vitro dissolution rates were determined according to Baggesen et al. (1981). The rotation speed was 30±1 r.p.m., and the dissolution medium was 25 ml of 0.1 M hydrochloric acid (pH 1.2), maintained at 37±0.1° C.

Release of propranolol into the dissolution medium was determined by means of UV spectrometry at 290 nm.

Release of potassium chloride into the dissolution medium was determined by means of a potassium-selective electrode.

Disintegration time of tablets was measured according to Ph.Eur. 2nd Ed. 1 V.5.1.1.

Tablet hardness was determined in a Schleuniger-2E apparatus (available from Dr. K. Schleuniger & Co., Switzerland) in kp.

The tabletting machine employed was an excenter press single-punch machine TM 20.

Calculation of the Dissolution Index (DI)

In the range of 20–80% drug released, an estimation was performed for at least four pairs of figures, e.g., $t_{20}$, $t_{35}$, $t_{50}$, $t_{65}$, of corresponding times for the two profiles so as to release the same amount of drug.

The correlated values were plotted in a time-time coordinate system, with the abscissa as time for the dissolution profile in simulated gastric fluid and the ordinate as the time in the simulated intestinal fluid.

A linear regression analysis was performed (at least four points, excluding 0.0). Provided that the shape of the two profiles are similar a straight line through the origin is achieved.

The dissolution index is calculated as:

$$DI = (b-1) \cdot 100$$

where b is the slope.

When the formulation dissolves faster in simulated intestinal fluid than in simulated gastric juice the calculated DI value will be negative.

The limit of pH-independency is a DI of $\leq 25$.

EXAMPLE 1

Preparation of Film-Coated Potassium Chloride Crystals

Preparation of Film-Coating Mixture

A film-coating mixture was prepared from the following ingredients:

| | |
|---|---|
| Eudragit ® E 30 D | 32.0% |
| Methocel ® E5 premium | 0.5% |
| Talc | 1.0% |
| Purified Water | to 100% (=11.1% dry matter) |

Water was heated to 80° C. and talc was dispersed therein by means of a disperser. To the heated mixture was added Methocel ® E5 premium which was dispersed in the form of discrete particles. This dispersion was slowly cooled to room temperature with stirring causing the HPMC to dissolve. The Eudragit ® E 30 D was added with stirring.

Application of Film-Coating Mixture on Potassium Chloride Crystals

The film-coating mixture prepared as described above at ambient temperature was sprayed onto potassium chloride crystals in a fluidized bed using an outlet air temperature of max. 40° C. The amount of film-coating mixture applied was 16.65% of dry matter by weight of the uncoated units.

Tabletting of Coated Potassium Chloride Crystals

The coated crystals prepared as described above were compressed to tablets with 25% of excipients in an excenter press single-punch tabletting machine TM 20 to a hardness of 7.0 kp (n=6). The resulting tablets had a gross weight of about 1200 mg, corresponding to 750 mg of KCl. The disintegration time of the tablets was 1.5 minutes.

The release of potassium was measured as described in MATERIALS AND METHODS:

TABLE 1

| Percentage of Potassium Released at pH = 1.2 (n = 3) after 1 hour | |
|---|---|
| Coated Crystals | 35.33 (s = 0.46) |
| Tablets | 34.10 (s = 0.52) |

It appears from Table 1 that there is no significant difference in the release of potassium from crystals and tablets, respectively, showing the compressibility of crystals coated with one layer of coating.

EXAMPLE 2

Preparation of Film-Coated Potassium Chloride Crystals

Preparation of Inner Film-Coating Mixture

An inner film-coating mixture was prepared from the following ingredients:

| | |
|---|---|
| Eudragit ® E 30 D | 43.3% |
| Methocel ® E5 | 0.65% |
| Talc | 1.35% |
| Purified Water | to 100% (=15% dry matter) |

The film-coating mixture was prepared and applied as described in Example 1.

Preparation of Outer Film-Coating Mixture

A film-coating mixture was prepared from the following ingredients:

| | |
|---|---|
| Methocel ® E5 premium | 6% |
| Talc | 6% |
| Purified water | 92% |
| | 100% (=12% dry matter) |

Water was heated to 80° C. and talc was dispersed therein by means of a disperser. To the heated mixture was added Methocel ® E5 premium which was dispersed in the form of discrete particles. This dispersion was slowly cooled to room temperature with stirring causing the HPMC to dissolve.

Application of Outer Film-Coating Mixture on Potassium Chloride Crystals

The outer film-coating mixture prepared as described above was sprayed onto the potassium chloride crystals already coated with the inner film layer in a fluidized bed using an outlet air temperature of max. 40° C. The outlet air temperature was then raised to 70° C. for 1 hour followed by cooling.

The amount of inner film layer applied was 13% and the amount of outer film layer was 1%, by weight of the uncoated crystals.

The release of potassium was measured as described in MATERIALS AND METHODS.

It appears from Table 2 that a prolonged dissolution profile has been obtained.

TABLE 2

| Percentage of Potassium Released at pH = 1.2 (n = 3) after | | |
|---|---|---|
| 1 h | 2 h | 6 h |
| 23.40 (s = 0.96) | 52.97 (s = 2.09) | 90.86 (s = 2.39) |

EXAMPLE 3

The Effect of Heating with Respect to the Dissolution Characteristics of the Film-Coated Crystals Inner and outer film-coating mixtures were prepared and applied as described in Example 1 and 2. In one experiment, no heating of the coated units took place.

The release of potassium was determined as described in MATERIALS AND METHODS.

TABLE 3

| Percentage of Potassium Released at pH = 1.2 after 1 hour (n = 3) | | |
|---|---|---|
| Time | 0 | 2 weeks |
| No heating | 41.85 | 37.14 |
|  | (s = 1.52) | (s = 2.73) |
| Heating at 70° C. for 1 h | 22.89 | 23.40 |
|  | (s = 0.87) | (s = 0.96) |

It appears from Table 3 that the release of potassium from the unheated units has decreased after two weeks, while remaining constant from the heat-treated units.

EXAMPLE 4

The Effect of Hydroxypropylmethylcellulose on the Release of Potassium from the Coated Crystals Preparation of Film-Coated Mixture Film-coating mixture were prepared from the following ingredients:

|  | A | B | C |
|---|---|---|---|
| Eudragit ® E 30 D | 44.3% | 43.2% | 41.5% |
| Methocel ® E5 prem. | 0.3% | 0.7% | 1.2% |
| Talc | 1.4% | 1.4% | 1.3% |
| Purified Water | to 100% (=15% dry matter) | to 100% (=15% dry matter) | to 100% (=15% dry matter) |

The film-coating mixtures were prepared and applied as described in Example 1 in an amount corresponding to 10% of the Eudragit ® E 30 D (dry matter).

The outer film-coating mixture was prepared and applied as described in Example 2.

The release of potassium chloride was measured as described in MATERIALS AND METHODS.

TABLE 4

| Percentage of Potassium Released at pH = 1.2 after 1 hour (n = 3) | | | |
|---|---|---|---|
| Film-coating mixture | A | B | C |
| Percent of HPMC[1] | 2.5 | 5 | 10 |
|  | 20.05 | 25.49 | 37.34 |
|  | (s = 0.31) | (s = 1.74) | (s = 1.04) |

[1]Calculated as dry matter on the amount of Eudragit ® and Methocel ®.

It appears from Table 4 that the release of potassium increases with the amount of HPMC added to the film-coating mixture. This means that HPMC should be incorporated in amounts which are sufficient to impart compressibility to the coating, but not sufficient to impair the release characteristics of the inner film layer.

EXAMPLE 5

The Effect of Different Amounts of Dry Matter on the Release of Potassium from Film-Coated Crystals Inner and outer film-coating mixtures were prepared as described in Example 1 and 2. The inner film-coating mixture was applied in varying amounts corresponding to 8%, 10%, 13% and 15% of dry matter, respectively. The outer film-coating mixture was applied as described in Example 2.

The release of potassium was measured as described in MATERIALS AND METHODS.

TABLE 5

| Percentage of Potassium Released at pH = 1.2 after 1 hour (n = 3) | | | | |
|---|---|---|---|---|
| Amount of inner film layer | 8% | 10% | 13% | 15% |
|  | 95.19 | 72.76 | 22.89 | 12.57 |
|  | (s = 1.13) | (s = 1.64) | (s = 0.87) | (s = 0.62) |

It appears from Table 5 that the release of potassium is correlated to the amount of inner film applied so that a reduction in release may be obtained by increasing the amount of inner film layer.

EXAMPLE 6

Tabletting of Coated Potassium Chloride Crystals

Coated potassium chloride crystals prepared as described in Example 1 and 2 were compressed to tablets with 27.3% of excipients as described in Example 1 to a hardness of 7.6 kp (n=6). The resulting tablets had a gross weight of about 1200 mg, corresponding to 750 mg of KCl. The disintegration time of the tablets was 3 minutes.

The release of potassium was measured as described in MATERIALS AND METHODS.

TABLE 6

|  | Percentage of Potassium Released at pH = 1.2 (n = 3) after | | |
|---|---|---|---|
|  | 1 h | 2 h | 6 h |
| Crystals | 23.40 | 52.97 | 90.86 |
|  | (s = 0.96) | (s = 2.09) | (s = 2.39) |
| Tablets | 22.89 | 54.42 | 94.30 |
|  | (s = 0.98) | (s = 1.45) | (s = 1.18) |

It appears from Table 6 that there is no significant difference in the release of potassium from crystals and tablets, respectively.

EXAMPLE 7

Preparation and Tabletting of Coated Cores

Preparation of Cores

Cores were prepared from the following ingredients:

| Propranolol hydrochloride | 60% |  |
|---|---|---|
| Microcrystalline cellulose | 22% |  |
| Sodiumdihydrogenphosphate | 15% |  |
| Sodiumcarboxymethylcellulose | 1% |  |
| Eudragit ® E 30 D | 2% | (dry matter) |
|  | 100% |  |

A mixture of the above ingredients was moistened with purified water and mixed until the mixture was a little grainy.

The moist mixture was extruded through a 0.75 mm sieve. The resulting extrudate consisted of strings breaking off in lengths of a few cm.

The extruded strings were formed into compact-shaped cores in a marumerizer. The resulting compact-shaped cores had a size of about 0.7–1.0 mm.

Inner and outer film-coating mixtures were prepared and applied as described in Example 2.

The coated cores were compressed into tablets with 40% of conventional excipients on the tabletting machine specified in MATERIALS AND METHODS.

The tablets had a weight of 500 mg, corresponding to 162.2 mg of propranolol hydrochloride per tablet.

Tablet harness was 6.3 kp when measured as described in MATERIALS AND METHODS.

The disintegration time was <1 minute.

The propranolol released was measured as described in MATERIALS AND METHODS.

TABLE 7

| | Percentage of propranolol released at pH = 1.2 (n = 3) after | | |
|---|---|---|---|
| | 1 h | 2 h | 6 h |
| Cores | 23.26 | 40.86 | 77.54 |
| | (s = 0.25) | (s = 0.64) | (s = 0.14) |
| Tablets | 27.28 | 45.79 | 79.74 |
| | (s = 0.92) | (s = 0.47) | (s = 1.46) |

| | Percentage of propranolol released at pH = 7.5 (n = 3) after | | |
|---|---|---|---|
| | 1 h | 2 h | 6 h |
| Cores | 28.75 | 51.30 | 82.00 |
| | (s = 0.11) | (s = 0.80) | (s = 0.56) |
| Tablets | 31.96 | 55.16 | 82.46 |
| | (s = 0.32) | (s = 0.35) | (s = 1.10) |

It appears from Table 7 that there is no significant difference in the release of propranolol from cores and tablets, respectively. The dissolution index is 4 determined as described in MATERIALS AND METHODS which means that the release is pH-independent.

EXAMPLE 8

The Effect of the Dry Matter Content in the Inner Film-Coating Mixture

Inner and outer film-coating mixtures were prepared and applied as described in Example 1 and 2 with the exception that the dry matter content of the inner film-coating mixture was 15%, 20%, 25%, and 30%, respectively, in different experiments.

All crystals were coated with 15% of dry matter relative to the weight of the uncoated crystals.

The release of potassium was measured as described in MATERIALS AND METHODS.

TABLE 8

| Percentage of Potassium Released at pH = 1.2 (n = 3) after | | | | |
|---|---|---|---|---|
| % of dry | 15 | 20 | 25 | 30 |
| matter | 23.13 | 21.58 | 29.06 | 27.57 |
| | (s = 0.82) | (s = 0.14) | (s = 0.53) | (s = 1.11) |

It appears from Table 8 that it is possible to use film-coating mixtures with as high a dry matter content as 30% without any significant change in release. This is important as a high dry matter content will lead to a shorter coating period.

LITERATURE

GB Patent No 1 468 172.

Eur. Patent Application No. 79 850 110, Publication No. 0 013 262.

U.S. Pat. No. 4,193,985.

Baggensen S, Bechgaard H, & Schmidt K, "Content and dissolution uniformity testing of controlled-release products: The Repro-Dose ® quality control procedure", *Pharm. Acta Helv* 56, 1981, pp. 85–92.

Bechgaard, H & Hegermann Nielsen, G, "Controlled release multiple units and single-units doses. A literature review", *Drug Develop Ind Pharm* 4, 1978, pp. 53–67.

Bechgaard, H & Ladefoged, K, "Distribution of pellets in the gastro-intestinal tract. The influence on transit time exerted by the density or diameter of pellets", *J Pharm Pharmacol* 30, 1978, pp. 690–692.

Bechgaard, H & Baggesen, S, "Propoxyphene and norpropoxyphene: Influence of type of controlled release formulation on intra- and intersubject variations", *J Pharm Sci* 69, 1980, pp. 1327–1330.

Bogentoft, C, Carlsson, Ekenved, G & Magnusson, A, "Influence of food on the absorption of acetylsalicylic acid from enteric-coated dosage forms", *Eur J Clin Pharmacol* 14, 1978, pp. 351–355.

Green, DM, "Tablets of coated aspirin microspherules—A new dosage form", *J New Drugs* 6, 1966, pp. 294–303.

McDonald, PJ, Mather, LE & Story, MJ, "Studies on absorption of a newly developed enteric-coated erythromycin base", *J Clin Pharmacol* 17, 1977, pp. 601–606.

Snedecor, GW & Cochran, WG, *Statistical Methods*, Iowa State University Press, Iowa, 1967, pp. 271–275.

We claim:

1. An oral pharmaceutical controlled release multiple-units formulation, comprising individual units constituted of an active substance coated with a substantially water-insoluble, but water-diffusible controlled release coating incorporating a homogeneous mixture of a water-dispersible film-forming agent and a polymeric substance which imparts compressibility to the coating.

2. A formulation according to claim 1 in which the film-forming agent is selected from cellulose derivatives, silicone polymers and copolymers, vinyl polymers and copolymers, biodegradable polymers selected from the group consisting of polyamino acids, polylactic acid and copolymers and derivatives thereof, or mixtures thereof.

3. A formulation according to claim 2 in which the film-forming agent is selected from ethyl cellulose and a copolymerisate of poly(meth)acrylic acid esters, hydroxypropylmethylcellulosephthalate, celluloseacetatephthalate, polyvinylacetatephthalate and vinylacetate-crotonic acid copolymerisates.

4. A formulation according to claim 2 in which the film-forming agent is a copolymerisate of acrylic acid ethylester and methacrylic acid methylester.

5. A formulation according to claim 1 in which the polymeric substance is selected from polyvinylpyrrolidone, polyalkylene glycols, and cellulose derivatives selected from the group consisting of hydroxypropylcellulose, carboxymethylcellulose, methylcellulose, propylcellulose, hydroxyethylcellulose, carboxyethylcellulose, carboxymethylhydroxyethylcellulose, hydroxymethylcellulose, carboxymethylethylcellulose, methylhydroxypropylcellulose and hydroxypropylmethylcellulose.

6. A formulation according to claim 5 in which the polymeric substance is present in an amount between 1 and 10% by weight relative to the amount of film-forming agent.

7. A formulation according to claim 1 in which the coating further comprises a finely divided, substantially water-insoluble, pharmaceutically acceptable, non-wetting anti-adhesive powder.

8. A formulation according to claim 7 in which the anti-adhesive is present in an amount of between about 1 and 50%, by weight of the coating.

9. A formulation according to claim 1 in which the units are crystals of a size between 0.1 and 1.5 mm.

10. A formulation according to claim 1 in which the units are cross-sectionally substantially homogeneous cores of a size of about 0.1–1.5 mm.

11. A formulation according to claim 1 in whcih the active substance in the units is potassium chloride.

12. A formulation according to claim 11 in which the units are potassium chloride crystals of a size of about 0.1–1.5 mm.

13. An oral pharmaceutical controlled release composition which comprises a multiplicity of units as specified in claim 1 admixed with one or more pharmaceutically acceptable fillers, diluents, binders, lubricants or disintegrants.

14. A pharmaceutical composition according to claim 13 which is a tablet which disintegrates upon ingestion in the stomach into a multiplicity of individual units.

15. A method of preparing an oral pharmaceutical controlled release multiple-units formulation as claimed in claim 1 comprising coating individual units containing an active substance with a mixture comprising an aqueous dispersion of a film-forming agent and a polymeric substance which prevents adhesion between the units and imparts compressibility to the coating.

* * * * *